United States Patent [19]

Van Eldik et al.

[11] Patent Number: 4,716,150

[45] Date of Patent: Dec. 29, 1987

[54] SYNTHETIC PEPTIDES AND USE THEREOF IN PREPARING CALMODULIN ANTISERA

[75] Inventors: Linda J. Van Eldik; D. Martin Watterson, both of Nashville, Tenn.

[73] Assignees: Vanderbilt University, Nashville, Tenn.; The Rockefeller University, New York, N.Y.

[21] Appl. No.: 770,227

[22] Filed: Aug. 26, 1985

Related U.S. Application Data

[63] Continuation of Ser. No. 597,243, Apr. 5, 1984, abandoned.

[51] Int. Cl.[4] .................... H61K 37/02; C07K 7/08; C07K 7/06
[52] U.S. Cl. ........................................ 514/14; 514/15; 514/16; 530/326; 530/327; 530/328
[58] Field of Search .......................... 514/14, 15, 16; 530/326, 327, 328

[56] References Cited

PUBLICATIONS

Watterson et al., (1976) J. Biol. Chem. 251 (15) 4501–4513.
Van Eldik, et al., (1981) J. Biol. Chem. 256 (9) 4205–4210.
Proceedings of the Nat'l. Acad. Sci. 80 (22) 1983 pp. 6775–6779.
European Journal of Biochem. 113, No. 2 (1981) 359–367.

Primary Examiner—Delbert R. Phillips
Attorney, Agent, or Firm—Tilton, Fallon, Lungmus & Chestnut

[57] ABSTRACT

The compounds of the present invention are synthetic peptides useful in developing antisera against vertebrate or plant calmodulins. The peptides have chain lengths of from 8 to 15 amino acids arranged in linear N-terminal to C-terminal sequences which include either the amino acid segment asparagine-tyrosine-glutamic acid-glutamic acid-phenylalanine-valine-glutamine, corresponding to a minimal immunoreactive site of vertebrate calmodulin, or the segment asparagine-tyrosine-glutamic acid-glutamic acid-phenylalanine-valine-lysine, corresponding to the analogous amino acid regin of plant calmodulin.

50 Claims, No Drawings

SYNTHETIC PEPTIDES AND USE THEREOF IN PREPARING CALMODULIN ANTISERA

GRANT REFERENCE

Research related to this invention was supported in part by grants from agencies of the U.S. Goverment; namely, under NIH Grant GM 30861 and NSF Grant PCM 8242875.

RELATED APPLICATION

This application is a continuation of copending application Ser. No. 597,243 filed Apr. 5, 1984, now abandoned.

BACKGROUND AND PRIOR ART

The use of synthetic peptide immunogens to produce antibodies of defined specificities is an important recent advance in immunochemistry. The present invention is directed to a group of synthetic peptide immunogens that can be used as reagents to elicit antisera against vertebrate or plant calmodulins.

Calmodulin and other members of the family of calcium-modulated proteins are major intracellular receptors for the element calcium, a substance of major importance in the regulation of many diverse cell processes such as motility, proliferation, and nutrient utilization. In addition, calcium is generally thought to be critical in the homeostasis of individual cells as well as whole organisms.

In order to elucidate the mechanisms of calcium control and the mechanisms of action of many hormones, regulatory agents, toxins, and pharmacological agents, it is necessary to examine cellular receptors for calcium, such as the protein calmodulin, and the means by which these receptors mediate the biological effects of calcium.

Calmodulin, a relatively small protein, exhibits multiple in vitro activities, although the physiological significance of a number of these activities remains obscure. However, calmodulin or calmodulin activity has been detected in most eukaryotic cells examined, and the amino acid sequence of the protein, as well as its in vitro activities, are highly conserved throughout vertebrate and invertebrate species, suggesting that calmodulin may play a fundamental role in mediating intracellular calcium-dependent effects.

Immunochemical techniques presently offer great potential for elucidating the exact role of calmodulin and other calcium-modulated proteins in cell function. For example, antisera elicited against calmodulin have become especially useful as immunodiagnostic reagents to differentially detect or purify calmodulin in supramolecular complexes. In addition, antisera of well-defined specificity are useful as molecular probes to define functional domains in calmodulin.

Unfortunately, our immunochemical studies on calmodulin were initially hindered by the inability to develop an anti-calmodulin serum of useful titer by merely injecting calmodulin into laboratory rabbits, a problem most likely resulting from the ubiquitous distribution of calmodulin throughout vertebrate and invertebrate species and the fact that its amino acid sequence differs minimally from species to species.

We overcame this problem in 1980 when, after testing a number of antigen modifications on calmodulin, we determined that the injection of performic acid-oxidized calmodulin into rabbits would result in antisera of useful titer reactive with either the oxidized or unoxidized molecule. Using one of the rabbit antisera, we proceeded to test peptide segments encompasssing the entire calmodulin molecule to locate one or more immunoreactive sites in the protein. See Van Eldik, L. J. and Watterson D. M. "Reproducible Production of Antiserum against Vertebrate Calmodulin and Determination of the Immunoreactive Site" *Journal of Biological Chemistry* Volume 256 (9), pp. 4205–4210 (1981). Upon completion of these studies we proposed than an immunoreactive site of calmodulin is contained in an 18 residue region (residues 127–144) within the COOH-terminal domain of calmodulin.

Further immunochemical studies of calmodulin involved our efforts to elucidate a specific and critical immunoreactive site within the proposed 18 residue region of the protein, the results of which were recently described in Van Eldik, et al. "Elucidation of a Minimal Immunoreactive Site of Vertebrate Calmodulin", *Archives of Biochemistry and Biophysics* Volume 227 (No. 2) pp. 522–533, (Dec. 1983). In this publication we reported that the heptapeptide segment asparagine-tyrosine-glutamic acid-glutamic acid-phenylalanine-valine-glutamine of vertebrate calmodulin (corresponding to amino acid residues 137 to 143) is as immunoreactive as the entire 148-residue protein with one antiserum. We also determined this heptapeptide segment to be the smallest calmodulin segment and the only 7-residue segment in region 135–145 of the protein capable of quantitive immunoreactivity with this anti-calmodulin serum. The analogous minimal immunoreactive site of plant calmodulin would be the heptapeptide segment asparagine-tyrosine-glutamic acid-glutamic acid-phenylalanine-valine-lysine, corresponding to residues 137–143 of the intact protein.

Recent advances in Immunochemistry involving the utilization of synthetic peptides to produce antibodies of defined specifities suggested the possibility that a synthetic peptide modeled after the immunoreactive-site heptapeptide of vertebrate or plant calmodulin would be effective as an immunogenic reagent to elicit antisera reactive with intact calmodulin. From a practical standpoint the ability to synthesize a peptide immunogen reagent as effective in eliciting anti-calmodulin serum as the protein itself, would greatly facilitate research in this area. Actual calmodulin is difficult to obtain, costly and in short supply.

In considering the possible design of a suitable peptide immunogen, we were guided in large part by the widely held assumption that a synthetic peptide containing an amino acid sequence corresponding to the immunoreactive region of a given protein will elicit antisera against the intact protein provided the peptide immunogen contains more than 6 amino acid residues, and provided the antigenic segment contained in the synthetic peptide would be surface-exposed if present in the actual protein from which it is derived. These prerequisites for the design of synthetic peptide immunogens were recently postulated by Lerner, R. A. (1982) *Nature* (London) Volume 299, pp. 592 to 596.

However, although the minimal immunoreactive heptapeptide site of calmodulin met both of the above requirements, we were unable to produce anti-calmodulin sera when we injected laboratory rabbits with a synthetic heptapeptide corresponding to the immunoreactive site of the protein. The synthetic heptapeptide was immunogenic in that it elicited an antibody response in the rabbits; however, the antibodies reacted with the synthetic heptapeptide but not with intact calmodulin. Van Eldik, et al. "Elucidation of a Minimal Immunoreactive Site of Vertebrate Calmodulin" (cited above). These findings suggested that the production of antisera against an intact protein using surface-exposed peptide regions is more complex than had been previously assumed.

Given our inability to use a synthetic version of the minimal immunoreactive site of calmodulin as an immunogen to elicit antisera against the whole molecule, we proposed that an effective design of synthetic peptide immunogens may require, in addition to minimum peptide length and surface exposure of the peptide segment in the intact protein, a presentation of the antigen region in the synthetic immunogen in an appropriate environment that most closely approximates the environment of the peptide segment within the intact protein.

SUMMARY OF THE INVENTION

The present invention is directed to an appropriate modification of the minimal immunoreactive-site heptapeptide of calmodulin sufficient to convert the segment into an immunogen reagent that will elicit antisera against intact calmodulin.

The invention involves a group of novel peptide immunogens effective as reagents for developing antisera against vertebrate or plant calmodulins. The peptide immunogens can be prepared by synthesizing chain lengths of from 8 to 15 amino acids arranged in linear N-terminal to C-terminal sequences which include either the peptide segment corresponding to the minimal immunoreactive site of vertebrate calmodulin, i.e., asparagine-tyrosine-glutamic acid-glutamic acid-phenylalanine-valine-glutamine, or including the peptide segment corresponding to the minimal immunoreactive site of plant calmodulin, i.e., the sequence asparagine-tyrosine-glutamic acid-glutamic acid-phenylalaninevaline-lysine.

Throughout the present disclosure, all of the amino acid sequences discussed correspond to sequences in actual vertebrate or plant calmodulins between and including residues 134 to 148 thereof, and should be understood by those skilled in the art as proceeding in sequence from N-terminal (134) to C-terminal (148) amino acids.

DESCRIPTION OF THE INVENTION

A synthetic peptide immunogen containing the minimal immunoreactive heptapeptide segment of vertebrate (or plant) calmodulin will elicit antisera reactive with intact calmodulin provided the synthetic peptide immunogen contains, in addition to the minimal immunoreactive sequence corresponding to residues 137 to 143 of vertebrate calmodulin (asparagine-tyrosine-glutamic acid-glutamic acid-phenylalanine-valine-lysine), at least one additional amino acid residue located either at the N-terminus or at the C-terminus of the reactive-site heptapeptides, the location and identity of this additional residue corresponding to that of residues 136 to 144 of vertebrate (or plant) calmodulin. Preferably, up to 3 additional residues are attached at the N-terminus of the reactive-site heptapeptides and/or up to 5 additional residues are attached at the C-terminus of the heptapeptides, the identity and sequence of these additional residues corresponding in identity and sequence, to the residues at positions 134 to 136 of vertebrate or plant calmodulin (if expanding the N-terminus of the reactive-site heptapeptides) and 144 to 148 (if expanding the C-terminus of the heptapeptides).

Vertebrate Synthetic Peptides

In one preferred embodiment, this invention comprises a class of synthetic peptide immunogens for use in developing antisera against vertebrate calmodulin, wherein the peptides have chain lengths of from 8 to 15 amino acids arranged in a linear N-terminal to C-terminal sequence, and which include the immunogenic heptapeptide segment asparagine-tyrosine-glutamic acid-glutamic acid-phenylalanine-valine-glutamine. More specifically, these vertebrate peptide immunogens comprise the following compounds:

(a) Gly-Gln-Val-Asn-Tyr-Glu-Glu-Phe-Val-Gln-Met-Met-Thr-Ala-Lys;
(b) Gly-Gln-Val-Asn-Tyr-Glu-Glu-Phe-Val-Gln-Met-Met-Thr-Ala;
(c) Gly-Gln-Val-Asn-Tyr-Glu-Glu-Phe-Val-Gln-Met-Met-Thr;
(d) Gly-Gln-Val-Asn-Tyr-Glu-Glu-Phe-Val-Gln-Met-Met;
(e) Gly-Gln-Val-Asn-Tyr-Glu-Glu-Phe-Val-Gln-Met;
(f) Gly-Gln-Val-Asn-Tyr-Glu-Glu-Phe-Val-Gln;
(g) Gln-Val-Asn-Tyr-Glu-Glu-Phe-Val-Gln-Met-Met-Thr-Ala-Lys;
(h) Gln-Val-Asn-Tyr-Glu-Glu-Phe-Val-Gln-Met-Met-Thr-Ala;
(i) Gln-Val-Asn-Tyr-Glu-Glu-Phe-Val-Gln-Met-Met-Thr;
(j) Gln-Val-Asn-Tyr-Glu-Glu-Phe-Val-Gln-Met-Met;
(k) Gln-Val-Asn-Tyr-Glu-Glu-Phe-Val-Gln-Met;
(l) Gln-Val-Asn-Tyr-Glu-Glu-Phe-Val-Gln;
(m) Val-Asn-Tyr-Glu-Glu-Phe-Val-Gln-Met-Met-Thr-Ala-Lys;
(n) Val-Asn-Tyr-Glu-Glu-Phe-Val-Gln-Met-Met-Thr-Ala;
(o) Val-Asn-Tyr-Glu-Glu-Phe-Val-Gln-Met-Met-Thr;
(p) Val-Asn-Tyr-Glu-Glu-Phe-Val-Gln-Met-Met;
(q) Val-Asn-Tyr-Glu-Glu-Phe-Val-Gln-Met;
(r) Val-Asn-Tyr-Glu-Glu-Phe-Val-Gln;
(s) Asn-Tyr-Glu-Glu-Phe-Val-Gln-Met-Met-Thr-Ala-Lys;
(t) Asn-Tyr-Glu-Glu-Phe-Val-Gln-Met-Met-Thr-Ala;
(u) Asn-Tyr-Glu-Glu-Phe-Val-Gln-Met-Met-Thr;
(v) Asn-Tyr-Glu-Glu-Phe-Val-Gln-Met-Met;
(w) Asn-Tyr-Glu-Glu-Phe-Val-Gln-Met

In the foregoing formulae, the abbreviations Gly, Gln, Val, Asn, Tyr, Glu, Phe, Met, Thr, Ala, and Lys represent respectively glycine, glutamine, valine, asparagine, tyrosine, glutamic acid, phenylalanine, methionine, threonine, alanine, and lysine. Cysteine may be added at either the N-terminal or the C-terminal ends of the above compounds (a) to (w).

Plant Synthetic Peptides

In another preferred embodiment, this invention comprises a class of synthetic peptide immunogens for use in developing antisera against plant calmodulin, wherein the peptides have chain lengths of from 8 to 15 amino acids arranged in a linear N-terminal to C-terminal sequence, and which includes the immunogenic heptapeptide segment asparagine-tyrosine-glutamic acid-glutamic acid-phenylalanine-valine-lysine. More specifically, these plant peptide immunogens comprise the following compounds:

(a) Gly-Gln-Ile-Asn-Tyr-Glu-Glu-Phe-Val-Lys-Val-Met-Met-Ala-Lys:

(b) Gly-Gln-Ile-Asn-Tyr-Glu-Glu-Phe-Val-Lys-Val-Met-Met-Ala;
(c) Gly-Gln-Ile-Asn-Tyr-Glu-Glu-Phe-Val-Lys-Val-Met-Met;
(d) Gly-Gln-Ile-Asn-Tyr-Glu-Glu-Phe-Val-Lys-Val-Met;
(e) Gly-Gln-Ile-Asn-Tyr-Glu-Glu-Phe-Val-Lys-Val;
(f) Gly-Gln-Ile-Asn-Tyr-Glu-Glu-Phe-Val-Lys;
(g) Gln-Ile-Asn-Tyr-Glu-Glu-Phe-Val-Lys-Val-Met-Met-Ala-Lys;
(h) Gln-Ile-Asn-Tyr-Glu-Glu-Phe-Val-Lys-Val-Met-Met-Ala;
(i) Gln-Ile-Asn-Tyr-Glu-Glu-Phe-Val-Lys-Val-Met-Met;
(j) Gln-Ile-Asn-Tyr-Glu-Glu-Phe-Val-Lys-Val-Met;
(k) Gln-Ile-Asn-Tyr-Glu-Glu-Phe-Val-Lys-Val;
(l) Gln-Ile-Asn-Tyr-Glu-Glu-Phe-Val-Lys;
(m) Ile-Asn-Tyr-Glu-Glu-Phe-Val-Lys-Val-Met-Met-Ala-Lys;
(n) Ile-Asn-Tyr-Glu-Glu-Phe-Val-Lys-Val-Met-Met-Ala;
(o) Ile-Asn-Tyr-Glu-Glu-Phe-Val-Lys-Val-Met-Met;
(p) Ile-Asn-Tyr-Glu-Glu-Phe-Val-Lys-Val-Met;
(q) Ile-Asn-Tyr-Glu-Glu-Phe-Val-Lys-Val;
(r) Ile-Asn-Tyr-Glu-Glu-Phe-Val-Lys;
(s) Asn-Tyr-Glu-Glu-Phe-Val-Lys-Val-Met-Met-Ala-Lys;
(t) Asn-Tyr-Glu-Glu-Phe-Val-Lys-Val-Met-Met-Ala;
(u) Asn-Tyr-Glu-Glu-Phe-Val-Lys-Val-Met-Met;
(v) Asn-Tyr-Glu-Glu-Phe-Val-Lys-Val-Met;
(w) Asn-Tyr-Glu-Glu-Phe-Val-Lys-Val.

In the foregoing formulae, the abbreviations Gly, Gln, Ile, Asn, Tyr, Glu, Phe, Val, Lys, Met, and Ala represent respectively glycine, glutamine, isoleucine, asparagine, tyrosine, glutamic acid, phenylalanine, valine, lysine, methionine, and adanine. Cysteine may be added at either the N-terminal or the C-terminal ends of any of the above compounds (a) to (w).

Prior to our synthesis of the present peptide immunogens, and in light of the formidable amount of immunochemical research that has yet to be completed in this area, it would have been rather difficult to predict with any certainty the type or degree of modification, if any, that would be capable of converting the immunoreactive heptapeptide segment of calmodulin into an effective synthetic immunogen for producing antisera against intact calmodulin.

We theorize here that the successful modification which we selected, namely, expansion of the heptapeptide segment by the attachment of at least one additional amino acid corresponding to an adjacent residue in the intact protein, may provide the resulting synthetic immunogen with an appropriate intramolecular environment allowing the critical peptide region contained within it to closely approximate the spacial orientation which it adopts in the intact protein.

The peptide immunogens of the present invention can be synthesized from their constituent amino acids using the Merrifield solid phase method as described in *Journal of the American Chemical Society*, Volume 85, pp. 2149–2154 (1963). This solid phase method for synthesizing sequences of amino acids is also described in Stewart and Young, *Solid Phase Peptide Synthesis* (W. H. Freeman and Co., San Francisco, 1969), pages 1–4. In this procedure, the C-terminal amino acid, such as lysine in peptide a of this invention is attached to chloromethylated polystyrenedivinylbenzene copolymer beads. Each subsequent amino acid, with suitable protecting group, is then added sequentially to the growing chain. For example as described in the Merrifield article, the protective group may be a carbobenzoxy group. Another commonly employed protecting group is a $N^a$-tert-butoxycarbonyl (abbreviated "Boc"). By the procedure of coupling, deprotection, and coupling of the next amino acid, the desired amino acid sequence and chain length can be produced. As a final step, the protective group is removed from the N-terminal residue, and the peptide is cleaved from the resin using a suitable reagent such as trifluoroacetic acid and hydrogen bromide.

To utilize the peptide immunogens of the present invention as reagents to elicit antisera against vertebrate or plant calmodulin, the peptides may be injected without a carrier protein or the peptides may be conjugated to a carrier protein such as KLH (keyhole limpet hemocyanin) or 2× crystallized ovalbumin by using iminothialane (King, T. P., Li, Y. and Kochoumian, L. 1978, *Biochemistry* 17: 1499–1506) or N-succinimidyl 3-(2-pyridylthio)propionate (SPDP) (Carlsson, J., Drevin, H. and Axen, R. 1977, *Biochem. J.* 173: 723–737). Conjugation of peptide to carrier protein may require adding a cysteinyl residue to the $NH_2$ terminus or COOH terminus of the peptide and coupling the Cys-peptide to the carrier protein through the thiol group of the cysteinyl residue.

For subcutaneous injection into laboratory rabbits the peptide or peptide-protein conjugates are emulsified in either complete Freund's adjuvant or incomplete Freund's adjuvant.

Procedures for preparing the peptide immunogens of the present invention, conjugating them to suitable carrier proteins, and injecting them into rabbits to elicit antisera, are further illustrated by the following example.

EXAMPLE I

Preparation and Injection of Peptide Immunogen Gly-Gln-Val-Asn-Tyr-Glu-Glu-Phe-Val-Gln-Met-Met-Thr-Ala-Lys The cys-pentadecapeptide immunogen is synthesized by the Merrifield solid phase method (Barany, G. and Merrifield, R. B. Solid-Phase Peptide Synthesis, in *The Peptides: Analysis, Synthesis, Biology* (eds. Gross, E. and Meienhofer, J.) Vol. 2, pp. 1–284 (1979) Academic Press, N.Y.) using a manually controlled shaker. The protecting group is $N^a$-tert-butoxycarbonyl (Boc). The peptide immunogen is prepared by stepwise addition of Boc-amino acids to $N^a$-Boc-$N^\epsilon$-(2-chlorobenzyloxycarbonyl)-L-lysine esterified to 4-hydroxyphenylacetamidomethyl-poly (styrene/1% divinylbenzene) beads (Mitchell, A. R., Erickson, B. W., Ryabtev, M. N., Hodges, R. S. and Merrifield, R. B. (1976) *J. Am. Chem. Soc.* 98: 7357–7362) at a loading of 0.32 mmol of lysine per gram of polystyrene. Each amino acid is added to the peptide chain using the following reaction cycle: Step 1, deprotection of the Boc-peptide-resin (1 equivalent) with 6.5M trifluoroacetic acid in dichloromethane for 1 min and then 30 min followed by washing four times with dichloromethane; twice with 2-propanol, and five times with dichloromethane; Step 2, neutralization with 0.5M N,N-diisopropylethylamine in dichloromethane for three 2-min periods followed by five dichloromethane washes; Step 3, coupling for 1 hr with the Boc-amino acid and N,N'-dicyclohexylcarbodiimide (3 equivalents each) followed by washing three times with dichloromethane, twice with 2-propanol, twice with dichloromethane, twice with 2-propanol, and five times with dichloromethane; Step 4, repetition of Step 2; and Step 5, repetition of Step 3. Additional coupling steps are not necessary. The peptide may be cleaved from the resin by treatment with 9 ml of anhydrous HF and 1 ml of anisole for 30 min while warming the reaction mixture from −70° to 0° C. After evaporation of the HF, the resin is washed with ether and the peptide is eluted with 20% (v/v) aqueous acetic acid.

Boc-asparagine and Boc-glutamine are coupled as their hydroxybenzotriazole esters, and step 3 is modified as follows: Boc-amino acid (4 equivalents) and 1-hydroxybenzotriazole (4 equivalents) in N,N-dimethylformamide are mixed at 0° C. for 10 min. N,N′-Dicyclohexylcarbodiimide (4 equivalents) in dichloromethane is precooled to 0° C. and added to the mixture. After 10 min, the mixture is filtered and the filtrate is shaken with the peptide resin for 1 hr. Material not coupled to the resin is removed by filtration and the peptide resin is washed three times with N,N-dimethylformamide, twice with 2-propanol, twice with dichloromethane, twice with 2-propanol, and five times with dichloromethane.

The peptide is purified by reverse-phase liquid chromatography on a column of octadecyl-silica. Homogeneity may be monitored by thin-layer chromatography and by amino acid analysis.

Prior to injection, the Cys-pentadecapeptide can be coupled to ovalbumin using SPDP essentially as described in Carlsson, J., Drevin, H. and Axen, R. (1977) *Biochem. J.* 173: 723–727. Briefly, after desalting on Sephadex G-25, 6.5 mg of ovalbumin in 0.8 ml of 0.01M sodium phosphate, pH 7.5, was mixed with 1.0 mg of SPDP in 0.2 ml of ethanol for 5 min. The reaction mixture was immediately passed through a column (0.9×25 cm) of Sephadex G-25 equilibrated in 0.01M sodium phosphate, pH 7.5. The fraction containing the activated ovalbumin (4 thiopyridine groups per molecule of ovalbumin) was mixed with 1.5 equivalents of the Cys-pentadecapeptide in 1.0 ml of 0.01M sodium phosphate, pH 7.5, for 24 hr at 25° C. Unreacted peptide and cross-linking reagent were removed by dialysis. Approximately 3.6 copies of the Cys-pentadecapeptide are conjugated to each mclecule of ovalbumin.

Injection Schedule. The peptide-protein conjugate containing the pentadecapeptide is emulsified in either complete Freund's adjuvant (initial injection) or incomplete Freund's adjuvant (subsequent injections). Injections are subcutaneous in 4 to 5 sites along the back of New Zealand White, Pasteurella-free, female rabbits. The subcutaneous injection in laboratory rabbits of the peptide immunogen-ovalbumin conjugate may proceed as follows: 50–60 nmol of peptide per rabbit per injection on days 0,14,16,18,21, and 23. The rabbits are then bled from the ear vein on day 30 and boosted approximately every 2 weeks and bled 7 to 10 days after each boost. Serum was obtained as described in Van Eldik, L. J. and Watterson, D. M. (1981) *J. Biol. Chem.* 256: 4205–4210.

We claim:

1. A synthetic peptide immunogen for use in developing antisera against vertebrate calmodulin, the peptides having a chain length of from 8 to 15 amino acids arranged in a linear N-terminal to C-terminal sequence which includes the immunogenic heptapeptide segment asparagine-tyrosine-glutamic acid-glutamic acid-phenylalanine-valine-glutamine, said peptide immunogen being selected from the class of peptides consisting of:
    (a) Gly-Gln-Val-Asn-Tyr-Glu-Glu-Phe-Val-Gln-Met-Met-Thr-Ala-Lys;
    (b) Gly-Gln-Val-Asn-Tyr-Glu-Glu-Phe-Val Gln-Met-Met-The-Ala;
    (c) Gly-Gln-Val-Asn-Tyr-Glu-Glu-Phe-Val-Gln-Met-Met-Thr;
    (d) Gly-Gln-Val-Asn-Tyr-Glu-Glu-Phe-Val-Gln-Met-Met;
    (e) Gly-Gln-Val-Asn-Tyr-Glu-Glu-Phe-Val-Gln-Met;
    (f) Gly-Gln-Val-Asn-Tyr-Glu-Glu-Phe-Val-Gln;
    (g) Gln-Val-Asn-Tyr-Glu-Glu-Phe-Val-Gln-Met-Met-Thr-Ala-Lys;
    (h) Gln-Val-Asn-Tyr-Glu-Glu-Phe-Val-Gln-Met-Met-Thr-Ala;
    (i) Gln-Val-Asn-Tyr-Glu-Glu-Phe-Val-Gln-Met-Met-Thr;
    (j) Gln-Val-Asn-Tyr-Glu-Glu-Phe-Val-Glu-Met-Met;
    (k) Gln-Val-Asn-Tyr-Glu-Glu-Phe-Val-Gln-Met;
    (l) Gln-Val-Asn-Tyr-Glu-Glu-Phe-Val-Gln;
    (m) Val-Asn-Tyr-Glu-Glu-Phe-Val-Gln-Met-Met-Thr-Ala-Lys;
    (n) Val-Asn-Tyr-Glu-Glu-Phe-Val-Gln-Met-Met-Thr-Ala;
    (o) Val-Asn-Tyr-Glu-Glu-Phe-Val-Gln-Met-Met-Thr;
    (p) Val-Asn-Tyr-Glu-Glu-Phe-Val-Gln-Met-Met;
    (q) Val-Asn-Tyr-Glu-Glu-Phe-Val-Gln-Met;
    (r) Val-Asn-Tyr-Glu-Glu-Phe-Val-Gln;
    (s) Asn-Tyr-Glu-Glu-Phe-Val-Gal-Met-Met-Thr-Ala-Lys;
    (t) Asn-Tyr-Glu-Glu-Phe-Val-Gln-Met-Met-Thr-Ala;
    (u) Asn-Tyr-Glu-Glu-Phe-Val-Gln-Met-Met-Thr;
    (v) Asn-Tyr-Glu-Glu-Phe-Val-Gln-Met-Met;
    (w) Ans-Tyr-Glu-Glu-Phe-Val-Gln-Met;
    wherein, optionally, cysteine may also be present at either the N-terminal or C-terminal ends of said compounds (a) to (w), and wherein the abreviations Gly, Gln, Val Asn, Tyr, Glu, Phe, Met, Thr, Ala, and Lys represent respectively glycine, glutamine, valine, asparagine, tyrosine, glutamic acid, phenylalanine, methionine, threonine, alanine, and lysine.

2. The synthetic peptide immunogen of claim 1 having the amino acid sequence (a).

3. The synthetic peptide immunogen of claim 1 having the amino acid sequence (b).

4. The synthetic peptide immunogen of claim 1 having the amino acid sequence (c).

5. The synthetic peptide immunogen of claim 1 having the amino acid sequence (d).

6. The synthetic peptide immunogen of claim 1 having the amino acid sequence (e).

7. The synthetic peptide immunogen of claim 1 having the amino acid sequence (f).

8. The synthetic peptide immunogen of claim 1 having the amino acid sequence (g).

9. The synthetic peptide immunogen of claim 1 having the amino acid sequence (h).

10. The synthetic peptide immunogen of claim 1 having the amino acid sequence (i).

11. The synthetic peptide immunogen of claim 1 having the amino acid sequence (j).

12. The synthetic peptide immunogen of claim 1 having the amino acid sequence (k).

13. The synthetic peptide immunogen of claim 1 having the amino acid sequence (l).

14. The synthetic peptide immunogen of claim 1 having the amino acid sequence (m).

15. The synthetic peptide immunogen of claim 1 having the amino acid sequence (n).

16. The synthetic peptide immunogen of claim 1 having the amino acid sequence (o).

17. The synthetic peptide immunogen of claim 1 having the amino acid sequence (p).

18. The synthetic peptide immunogen of claim 1 having the amino acid sequence (q).

19. The synthetic peptide immunogen of claim 1 having the amino acid sequence (r).

20. The synthetic peptide immunogen of claim 1 having the amino acid sequence (s).

21. The synthetic peptide immunogen of claim 1 having the amino acid sequence (t).

22. The synthetic peptide immunogen of claim 1 having the amino acid sequence (u).

23. The synthetic peptide immunogen of claim 1 having the amino acid sequence (v).

24. The synthetic peptide immunogen of claim 1 having the amino acid sequence (w).

25. A synthetic peptide immunogen for use in developing antisera against plant calmodulin, the peptide having a chain length of from 8 to 15 amino acids arranged in a linear N-terminal to C-terminal sequence which includes the immunogenic heptapeptide segment asparagine-tyrosine-tyrosine-glutamic acid-glutamic acid-phenylalanine-valine-lysine, said peptide immunogen being selected from the class of peptides consising of:

(a) Gly-Gln-Ile-Asn-Tyr-Glu-Glu-Phe-Val-Lys-Met-Met-Ala-Lys;
(b) Gly-Gln-Ile-Asn-Tyr-Glu-Glu-Phe-Val-Lys-Val-Met-Met-Ala;
(c) Gly-Gln-Ile-Asn-Tyr-Glu-Glu-Phe-Val-Lys-Val-Met-Met;
(d) Gly-Gln-Ile-Asn-Tyr-Glu-Glu-Phe-Val-Lys-Val-Met;
(e) Gly-Gln-Ile-Asn-Tyr-Glu-Glu-Phe-Val-Lys-Val;
(f) Gly-Gln-Ile-Asn-Tyr-Glu-Glu-Phe-Val-Lys;
(g) Gln-Ile-Asn-Tyr-Glu-Glu-Phe-Val-Lys-Val-Met-Met-Ala-Lys;
(h) Gln-Ile-Asn-Tyr-Glu-Glu-Phe-Val-Lys-Val-Met-Met-Ala;
(i) Gln-Ile-Asn-Tyr-Glu-Glu-Phe-Val-Lys-Val-Met-Met;
(j) Gln-Ile-Asn-Tyr-Glu-Glu-Phe-Val-Lys-Val-Met;
(k) Gln-Ile-Asn-Tyr-Glu-Glu-Phe-Val-Lys-Val;
(l) Gln-Ile-Asn-Tyr-Glu-Glu-Phe-Val-Lys;
(m) Ile-Asn-Tyr-Glu-Glu-Phe-Val-Lys-Val-Met-Met-Ala-Lys;
(n) Ile-Asn-Tyr-Glu-Glu-Phe-Val-Lys-Val-Met-Met-Ala;
(o) Ile-Asn-Tyr-Glu-Glu-Phe-Val-Lys-Val-Met-Met;
(p) Ile-Asn-Tyr-Glu-Glu-Phe-Val-Lys-Val-Met;
(q) Ile-Asn-Tyr-Glu-Glu-Phe-Val-Lys-Val;
(r) Ile-Asn-Tyr-Glu-Glu-Phe-Val-Lys;
(s) Asn-Tyr-Glu-Glu-Phe-Val-Lys-Val-Met-Met-Ala-Lys;
(t) Asn-Tyr-Glu-Glu-Phe-Val-Lys-Val-Met-Met-Ala;
(u) Asn-Tyr-Glu-Glu-Phe-Val-Lys-Val-Met-Met;
(v) Asn-Tyr-Glu-Glu-Phe-Val-Lys-Val-Met;
(w) Asn-Tyr-Glu-Glu-Phe-Val-Lys-Val;

wherein, optionally, cysteine may also be present at either the N-terminal or C-terminal ends of said complexes (a) to (w) and wherein the abbreviations Gly, Gln, Ile, Asn, Tyr, Glu, Phe, Val, Lys, Met, and Ala represent repectively glycine, glutamine, isoleucine, asparagine tyrosine, glutamic acid, phenylalanine, valine, lysine, methionine and alanine.

26. The synthetic peptide immunogen of claim 25 having the amino acid sequence (a).

27. The synthetic peptide immunogen of claim 25 having the amino acid sequence (b).

28. The synthetic peptide immunogen of claim 25 having the amino acid sequence (c).

29. The synthetic peptide immunogen of claim 25 having the amino acid sequence (d).

30. The synthetic peptide immunogen of claim 25 having the amino acid sequence (e).

31. The synthetic peptide immunogen of claim 25 having the amino acid sequence (f).

32. The synthetic peptide immunogen of claim 25 having the amino acid sequence (g).

33. The synthetic peptide immunogen of claim 25 having the amino acid sequence (h).

34. The synthetic peptide immunogen of claim 25 having the amino acid sequence (i).

35. The synthetic peptide immunogen of claim 25 having the amino acid sequence (j).

36. The synthetic peptide immunogen of claim 25 having the amino acid sequence (k).

37. The synthetic peptide immunogen of claim 25 having the amino acid sequence (l).

38. The synthetic peptide immunogen of claim 25 having the amino acid sequence (m).

39. The synthetic peptide immunogen of claim 25 having the amino acid sequence (n).

40. The synthetic peptide immunogen of claim 25 having the amino acid sequence (o).

41. The synthetic peptide immunogen of claim 25 having the amino acid sequence (p).

42. The synthetic peptide immunogen of claim 25 having the amino acid sequence (q).

43. The synthetic peptide immunogen of claim 25 having the amino acid sequence (r).

44. The synthetic peptide immunogen of claim 25 having the amino acid sequence (s).

45. The synthetic peptide immunogen of claim 25 having the amino acid sequence (t).

46. The synthetic peptide immunogen of claim 25 having the amino acid sequence (u).

47. The synthetic peptide immunogen of claim 25 having the amino acid sequence (v).

48. The synthetic peptide immunogen of claim 25 having the amino acid sequence (w).

49. The method of preparing vertebrate calmodulin antisera wherein one of the peptide compounds of claim 1 is injected into a laboratory animal suitable for use in preparing antisera.

50. The method of preparing plant calmodulin antisera wherein one of the peptide compounds of claim 25 is injected into a laboratory animal suitable for preparing antisera.

* * * * *

UNITED STATES PATENT AND TRADEMARK OFFICE
CERTIFICATE OF CORRECTION

PATENT NO. : 4,716,150

DATED : December 29, 1987

INVENTOR(S) : Linda J. Van Eldik; D. Martin Watterson.

It is certified that error appears in the above-identified patent and that said Letters Patent is hereby corrected as shown below:

On the Title Page, Item [75] should read:

Inventors:

Linda J. Van Eldik; D. Martin Watterson, both of Nashville, Tenn; Bruce W. Erickson, Coster, N.J.; Kam-Fook Fok, St. Louis, Mo.

Signed and Sealed this

Seventeenth Day of May, 1988

Attest:

DONALD J. QUIGG

*Attesting Officer*  *Commissioner of Patents and Trademarks*